(12) United States Patent
Williams (10) Patent No.: US 10,213,438 B2
(45) Date of Patent: Feb. 26, 2019

(54) ALKALOID COMPOUNDS FOR TREATING DEPRESSION, SUBSTANCE ADDICTIONS, AND INDICATIONS ASSOCIATED WITH CHRONIC INFLAMMATION

(71) Applicant: MyMD Pharmaceuticals, Inc., Tampa, FL (US)

(72) Inventor: Jonnie R. Williams, Sarasota, FL (US)

(73) Assignee: MyMD Pharmaceuticals, Inc., Tampa, FL (US)

(*) Notice: Subject to any disclaimer, the term of this patent is extended or adjusted under 35 U.S.C. 154(b) by 72 days.

(21) Appl. No.: 15/522,815

(22) PCT Filed: Nov. 16, 2015

(86) PCT No.: PCT/US2015/060887
§ 371 (c)(1),
(2) Date: Apr. 28, 2017

(87) PCT Pub. No.: WO2016/081369
PCT Pub. Date: May 26, 2016

(65) Prior Publication Data
US 2018/0271875 A1 Sep. 27, 2018

Related U.S. Application Data (60) Provisional application No. 62/081,125, filed on Nov. 18, 2014.

(51) Int. Cl.
| | | |
|---|---|---|
| *A61K 31/55* | (2006.01) | |
| *C07D 401/04* | (2006.01) | |
| *A61P 37/02* | (2006.01) | |
| *A61P 35/00* | (2006.01) | |
| *A61K 31/4439* | (2006.01) | |
| *A61K 31/444* | (2006.01) | |

(52) U.S. Cl.
CPC ............ *A61K 31/55* (2013.01); *A61K 31/444* (2013.01); *A61K 31/4439* (2013.01); *A61P 35/00* (2018.01); *A61P 37/02* (2018.01); *C07D 401/04* (2013.01)

(58) Field of Classification Search
None
See application file for complete search history.

(56) References Cited

U.S. PATENT DOCUMENTS

| | | |
|---|---|---|
| 3,901,248 A | 8/1975 | Lichtneckert et al. |
| 5,942,244 A | 8/1999 | Friedman et al. |
| 6,350,479 B1 | 2/2002 | Williams et al. |
| 8,609,708 B2 | 12/2013 | Cashman |
| 2012/0245202 A1 | 9/2012 | Williams |

FOREIGN PATENT DOCUMENTS

| | | |
|---|---|---|
| EP | 0421762 A1 | 4/1991 |
| WO | 98/054152 A1 | 12/1998 |

OTHER PUBLICATIONS

Jul. 28, 2016—International Search Report and Written Opinion—PCT/US2015/060887.
Wang, D. X. et al., "Structure-activity relationships for nicotine analogs comparing competition for [3H]nicotine binding and psychotropic potency", Drug Development Research, 1998, vol. 45, No. 1, pp. 10-16.
Nenajdenko, V. G. et al., "A novel convenient approach to the synthesis of 2-substituted analogs of ornithine and homolysine", Russian Chemical Bulletin, Int. Ed., 2004, vol. 53, No. 12, pp. 2866-2870.
Shevchenko, N. E. et al., "The reaction of cyclic imines with the Ruppert-Prakash reagent. Facile approach to alpha-trifluoromethylated nomicotine, anabazine, and homoanabazine", Tetrahedron, 2011, vol. 67, pp. 69-74.
Liu, X. et al., "Studies on the Pyrrolinone Metabolites Derived from the Tobacco Alkaloid 1-Methyl-2-(3-pyridinyl) pyrrole (beta-nicotyrine)", Chem. Res. Toxicol., 1999, vol. 12, No. 6, pp. 508-512.
Shigenaga, M. K. et al., "Liver and lung microsomal metabolism of the tobacco alkaloid β-nicotyrine", Chem. Res. Toxicol., 1989, vol. 2, No. 5, pp. 282-287.
Chemical Abstract compounds, STN express, RN 31738-15-5 (Entered STN: Nov. 16, 1984).
A.A. Boulton et al., "Biogenic Amine Adducts, Monoamine Oxidase Inhibitors, and Smoking," Lancet, 1 (8577):114-155 (1988).
L.A. Carr et al., "Effects of Tobacco Smoke Constituents on MPTP Induced Toxicity and Monoamine Oxidase Activity in the Mouse Brain," Life Sciences, 48:1173 1177 (1991).
J.S. Fowler et al., "Inhibition of Monoamine Oxidase B in the Brain of Smokers," Nature (London), 379(6567): 733 736 (1996).
J. Stephenson, "Clues Found to Tobacco Addiction," Journal of the American Medical Association, 275(16): 1217 1218 (1996).
P. H. Stahl et al., Handbook of Pharmaceutical Salts: Properties, Selection and Use, Weinheim/Zürich:Wiley-VCH/VHCA, 2002.

*Primary Examiner* — Bong-Sook Baek
(74) *Attorney, Agent, or Firm* — Banner & Witcoff, Ltd.

(57) ABSTRACT

Alkaloid compounds described herein are useful for treating disorders associated with monoamine oxidase (MAO) activity, such as depression, pain, smoking cessation, and substance addictions, and/or for treating disorders associated with chronic or low-level inflammation. In some examples, compounds are effective for treating cancers, autoimmune disorders, and other disorders associated with inducible nitric oxide synthase (iNOS).

5 Claims, 3 Drawing Sheets

ALKALOID COMPOUNDS FOR TREATING DEPRESSION, SUBSTANCE ADDICTIONS, AND INDICATIONS ASSOCIATED WITH CHRONIC INFLAMMATION

CROSS REFERENCE TO RELATED APPLICATION

This application is a U.S. National Stage application under 35 U.S.C. § 371 of International Application PCT/US2015/060887 (published as WO 2016/081369 A1), filed Nov. 16, 2015, claims priority to U.S. provisional application No. 62/081,125, filed Nov. 18, 2014, the disclosure of which is hereby incorporated by reference in its entirety.

BACKGROUND

Monoamine oxidase (MAO) inhibitors can regulate the level of monoamines and their neurotransmitter release in different brain regions and in the body (including dopamine, norepinephrine, and serotonin). MAO inhibitors (MAOI) can thereby affect the modulation of neuroendocrine function, respiration, mood, motor control and function, focus and attention, concentration, memory and cognition, and the mechanisms of substance abuse. MAOI have been demonstrated to have effects on attention, cognition, appetite, substance abuse, memory, cardiovascular function, extrapyramidal function, pain and gastrointestinal motility and function. The distribution of MAO in the brain is widespread and includes the basal ganglia, cerebral cortex, limbic system, and mid and hind-brain nuclei. In the peripheral tissue, the distribution includes muscle, the gastrointestinal tract, the cardiovascular system, autonomic ganglia, the liver, and the endocrinic system. Regulation of monoamine levels in the body has been shown to be effective in numerous disease states including depression, anxiety, stress disorders, and withdrawal symptoms, among others.

It has been suggested that cigarette smoke may have irreversible inhibitory effect towards monoamine oxidase (MAO). A. A. Boulton et al., "Biogenic Amine Adducts, Monoamine Oxidase Inhibitors, and Smoking," Lancet, 1 (8577):114-155 (1988), reported that the MAO-inhibiting properties of cigarette smoke may help to explain the protective action of smoking against Parkinson's disease and also observed that patients with mental disorders who smoke heavily do not experience unusual rates of smoking-induced disorders. It was suggested that smoking, as an MAOI, may protect against dopaminergic neurotoxicity that leads to Parkinson's disease and that the MAO-inhibiting properties of smoking may result in an anti-depressive effect in mental patients.

L. A. Carr et al., "Effects of Tobacco Smoke Constituents on MPTP Induced Toxicity and Monoamine Oxidase Activity in the Mouse Brain," Life Sciences, 48:1173-1177 (1991), found that nicotine, 4-phenylpyridine and hydrazine prevented the decrease in dopamine metabolite levels induced by 1-methyl-4-phenyl-1,2,3,6-tetrahydropyridine (MPTP) in mice, but there was no significant effect on dopamine levels. Because tobacco smoke particulate matter caused a marked inhibition of MAO-A and MAO-B activity when added in vitro, it was suggested that one or more unidentified substances in tobacco smoke are capable of inhibiting brain MAO and perhaps altering the formation of the active metabolite of MPTP.

J. S. Fowler et al., "Inhibition of Monoamine Oxidase B in the Brain of Smokers," Nature (Lond), 379(6567): 733-736 (1996), found that the brains of living smokers showed a 40% decrease in the level of MAO-B relative to non-smokers or former smokers. MAO inhibition was also reported as being associated with decreased production of hydrogen peroxide.

It has also been suggested that nicotine may not be the only constituent of tobacco responsible for tobacco addiction. J. Stephenson, "Clues Found to Tobacco Addiction," Journal of the American Medical Association, 275(16): 1217-1218 (1996), discussing the work of Fowler, et al., pointed out that the brains of living smokers had less MAO-B compared with the brains of nonsmokers or former smokers. MAO-B is an enzyme involved in the breakdown of dopamine, which is a pleasure-enhancing neurotransmitter. The results suggested that the inhibition of MAO-B in the brains of smokers may make nicotine more addictive by slowing down the breakdown of dopamine, thereby boosting its levels. The findings provided an explanation as to why cigarette smokers were less susceptible to developing Parkinson's disease. Further, the findings suggested that MAOI could be used for smoking cessation. Williams et al. U.S. Pat. No. 6,350,479 reported that the minor tobacco alkaloids anabasine, anatabine, and nornicotine exhibited MAO inhibitory effects against MAO-A and MAO-B.

Inflammation is a protective response to harmful stimuli, such as oxidative stress, irritants, pathogens, and damaged cells. The inflammatory response involves the production and release of inflammatory modulators that heal injured tissue and destroy damaged cells, by directly or indirectly producing and/or signaling the release of agents that produce reactive oxygen species. Thus, an appropriate inflammatory response involves a balance between the destruction of damaged cells and the healing of injured tissue.

Some anti-inflammatory compounds function by reducing transcription mediated by nuclear factor κB (NFκB). NFκB is a transcription factor which operates in cells involved in inflammatory and immune reactions. NFκB-mediated transcription is associated with numerous disorders including, for example, immune or autoimmune disorders, arthritis, various cancers, upper respiratory tract infections, neurodegenerative diseases, and so forth. Williams U.S. 2012/0245202 reported that anatabine is effective for treating disorders having a NFκB-mediated inflammatory component.

The role of nitric oxide (NO) in tumorigenesis has been well-studied. A large majority of human tumors appear to progress owing to NO resulting from inducible nitric oxide synthase (iNOS), further stimulated by pro-inflammatory cytokines. Conversely, in some cases, NO is associated with induction of apoptosis and tumor regression. This dichotomy of NO is attributable to the complexity of signaling pathways in tumor cells, which may respond to NO very differently depending on concentration. Also, NO alters many signaling pathways through chemical modifications, such as the addition of S-nitrosothiols and nitrosotyrosine to target proteins altering various biological pathways. As a consequence, iNOS inhibitors have been designed and developed to inhibit various organ site cancers including the colon.

It would be desirable to develop alternative compounds for treating indications such as depression, substance addiction, smoking cessation, pain, and/or disorders associated with chronic inflammation.

SUMMARY

This disclosure describes alkaloid compounds which may be useful for treating smoking cessation, depression, substance addiction, pain, and/or disorders associated with chronic or low-level inflammation, including disorders having a NFκB-mediated inflammatory component. In some examples, the compounds are useful for treating disorders associated with monoamine oxidase (MAO) activity and/or inducible nitric oxide synthase (iNOS).

In another aspect, a composition comprises a therapeutically effective dose of a certain alkaloid compound or a pharmaceutically acceptable salt thereof and a pharmaceutically acceptable vehicle therefor.

BRIEF DESCRIPTION OF THE DRAWINGS

A more complete understanding of the present invention and certain advantages thereof may be acquired by referring to the following detailed description in consideration with the accompanying drawings, in which.

DETAILED DESCRIPTION

The compounds useful for treating smoking cessation, depression, substance addiction, pain, and/or disorders associated with chronic or low-level inflammation may a structure selected from the following.

1-Methyl-2,3-dihydro-1H-[2,3']bipyridinyl-6-one

Other examples of alkaloid compounds include 3,4,5,6-tetrahydro-[2,3'] bipyridinyl and 3,6-dihydro-[2,3']bipyridinyl. In some embodiments, the compounds may be adsorbed on a cation exchange resin such as polymethacrilic acid (Amberlite IRP64 or Purolite C115HMR), as described in U.S. Pat. No. 3,901,248, the entire disclosure of which is hereby incorporated by reference in its entirety. Such cation exchange resins have been used commercially, for example, in nicotine replacement therapy, e.g., nicotine polacrilex.

Compounds also may be formed as salts, which may be helpful to improve chemical purity, stability, solubility, and/or bioavailability. Non-limiting examples of possible salts are described in P. H. Stahl et al., *Handbook of Pharmaceutical Salts: Properties, Selection and Use*, Weinheim/Zürich:Wiley-VCH/VHCA, 2002, including salts of 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p), and undecylenic acid.

Compounds described herein may be prepared synthetically, for example using one of the reaction schemes illustrated below or by other suitable pathways that will be apparent to persons skilled in the art. By way of non-limiting example, compounds described herein may be synthesized according to one of the following pathways illustrated in Cashman U.S. Pat. No. 8,609,708, the disclosure of which is hereby incorporated by reference in its entirety.

Compounds intended for administration to humans or other mammals generally should have very high purity. In the case of synthetically prepared compounds, purity refers to the ratio of a compound's mass to the total sample mass following any purification steps. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

Compounds described herein that exist in more than one optical isomer form (enantiomers) may be provided either as racemic mixture or by isolating one of the enantiomers, the latter case in which purity as described above may refer to enantiomeric purity.

While not wanting to be bound by theory, compounds disclosed herein may exhibit properties as inhibitors of monoamine oxidase (MAO) activity, including either or both of MAO-A and MAO-B activity. These properties may enable compounds to be effective for treating indications associated with MAO activity, such as depression, pain, substance addiction, smoking cessation, and the like. Compounds disclosed herein also (or alternatively) may exhibit anti-inflammatory properties owing to the compound's interaction with inflammation pathways, including by way of example, interleukins such as IL-1 and IL-6, TNF, cyclooxygenase (COX), and the like. A compound's ability to inhibit MAO-A and/or MAO-B activity, and/or its ability to inhibit COX and/or other pathways associated with inflammation may be evaluated using assays well known to persons of ordinary skill in the art.

Hydrogen peroxide ($H_2O_2$) is a stable, uncharged and freely diffusable reactive oxygen species (ROS) and second messenger. The generation of $H_2O_2$ in the brain is especially high because of the high oxygen consumption in the tissue. ROS are essentially produced by mitochondria, and the ability to block mitochondrial enzymes such as MAO may prevent early stage $H_2O_2$ production. In some examples, the compounds disclosed herein may specifically target $H_2O_2$, such as by inhibiting the synthesis of $H_2O_2$, thereby modulating $H_2O_2$ levels to treat a variety of disorders associated with elevated levels of $H_2O_2$.

The compounds disclosed herein also (or alternatively) may exhibit properties as inhibitors of inducible nitric oxide synthase (iNOS). Such properties may enable the compounds to be effective in the treatment of cancers or tumors including leukemia, e.g., acute leukemia, acute lymphocytic leukemia, acute myelocytic leukemia, such as myeloblastic, promyelocytic, myelomonocytic, monocytic, and erythroleukemia leukemia, and myelodysplastic syndrome; chronic leukemia, such as chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as smoldering multiple myeloma, nonsecretory myeloma, osteo sclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as pheochromocytom and adrenocortical carcinoma; thyroid cancer such as papillary or follicular thyroid cancer, medullary thyroid cancer and anaplastic thyroid cancer; pancreatic cancer such as insulinoma, gastrinoma, glucagonoma, vipoma, somatostatin-secreting tumor, and carcinoid or islet cell tumor; pituitary cancers such as Cushing's disease, prolactin-secreting tumor, acromegaly, and diabetes insipius; eye cancers such as ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as squamous cell carcinoma, and adenocarcinoma; uterine cancers such as endometrial carcinoma and uterine sarcoma; ovarian cancers such as ovarian epithelial carcinoma, borderline tumor, germ cell tumor, and stromal tumor; esophageal cancers such as squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as hepatocellular carcinoma and hepatoblastoma; gallbladder cancers such as adenocarcinoma; cholangiocarcinomas such as pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as germinal tumor, seminoma, anaplastic, classic (typical), spermatocytic, nonseminoma, embryonal carcinoma, teratoma carcinoma, choriocarcinoma (yolk-sac tumor), prostate cancers such as prostatic intraepithelial neoplasia, adenocarcinoma, leiomyosarcoma, and rhabdomyosarcoma; penal cancers; oral cancers such as squamous cell carcinoma; basal cancers; salivary gland cancers such as adenocarcinoma, mucoepidermoid carcinoma, and adenoidcystic carcinoma; pharynx cancers such as squamous cell cancer, and verrucous; skin cancers such as basal cell carcinoma, squamous cell carcinoma and melanoma, superficial spreading melanoma, nodular melanoma, lentigo malignant melanoma, acral lentiginous melanoma; kidney cancers such as renal cell carcinoma, adenocarcinoma, hypemephroma, fibrosarcoma, transitional cell cancer (renal pelvis and/or uterer); Wilms' tumor; bladder cancers such as transitional cell carcinoma, squamous cell cancer, adenocarcinoma, carcinosarcoma. Other types of cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

Compounds disclosed herein may be useful in the treatment of a variety of cancers or other abnormal proliferative diseases, such as carcinoma, including that of the bladder, breast, prostate, rectal, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoictic tumors of myeloid lineage, including acute and chronic myelogenous leukemias and promyclocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. Cancers caused by aberrations in apoptosis also may be treated. Such cancers may include follicular lymphomas, hormone dependent tumors of the breast, prostate and ovary, and precancerous lesions such as familial adenomatous polyposis, and myelodysplastic syndromes. In some examples, malignancy or dysproliferative changes, e.g., metaplasias and dysplasias), or hyperproliferative disorders, may be treated in the skin, lung, colon, rectum, breast, prostate, bladder, kidney, pancreas, ovary, or uterus. In other examples, sarcoma, melanoma, small lung carcinoma, or leukemia may be treated.

In other aspects, compounds disclosed herein may be useful for treating autoimmune disorders. An autoimmune disorder occurs when the body's immune system attacks and destroys healthy body tissue by mistake. Though the exact cause of autoimmune disorders is unknown, it is theorized that some microorganisms (such as bacteria or viruses) or drugs may trigger changes that confuse the immune system. Genetic factors may make some individuals more prone to autoimmune disorders. Non-limiting examples of autoimmune disorders include Addison's disease, Celiac disease (gluten-sensitive enteropathy), dermatomyositis, Graves' disease, Hashimoto's thyroiditis, multiple sclerosis, myasthenia gravis, pernicious anemia, reactive arthritis, rheumatoid arthritis, Sjogren syndrome, systemic lupus erythematosus, and Type I diabetes.

Suitable doses may vary over a wide range depending on a variety of factors including the type and/or severity of the disease or disorder, previous treatments, the general health, age, and/or weight of the individual, the frequency of treatments, the rate of release from the composition, and other diseases present. This dose may vary according to factors such as the disease state, age, and weight of the subject. For example, higher doses may be administered for treatments involving conditions which are at an advanced stage and/or life-threatening. Dosage regimens also may be adjusted to provide the optimum therapeutic response.

Pharmaceutical Compositions

Pharmaceutical compositions may be formulated together with one or more acceptable pharmaceutical or food grade carriers or excipients. As used herein, the term "acceptable pharmaceutical or food grade carrier or excipient" means a non-toxic, inert solid, semisolid or liquid filler, diluent, encapsulating material or formulation auxiliary of any type. For example, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions may be prepared by any suitable technique and is not limited by any particular method for its production. For example, myosmine can be combined with excipients and a binder, and then granulated. The granulation can be dry-blended with any remaining ingredients, and compressed into a solid form such as a tablet.

Pharmaceutical compositions may be administered by any suitable route. For example, the compositions may be administered orally, parenterally, by inhalation spray, topically, rectally, nasally, buccally, vaginally, via an implanted reservoir, or ingested as a dietary supplement or food. In some embodiments, a composition is provided in an inhaler, which may be actuated to administer a vaporized medium that is inhaled into the lungs. The term parenteral as used herein includes subcutaneous, intracutaneous, intravenous, intramuscular, and intracranial injection or infusion techniques. Most often, the pharmaceutical compositions are readily administered orally and ingested.

Pharmaceutical compositions may contain any conventional non-toxic pharmaceutically-acceptable carriers, adjuvants or vehicles. In some cases, the pH of the formulation may be adjusted with acceptable pharmaceutical or food grade acids, bases or buffers to enhance the stability of the formulated composition or its delivery form.

Liquid dosage forms for oral administration include acceptable pharmaceutical or food grade emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylsulfoxide (DMSO) dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, lozenges, pills, powders, and granules. In such solid dosage forms, the active compound is mixed with at least one inert, acceptable pharmaceutical or food grade excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agaragar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, i) lubricants such as talc, calcium stearate, magnesium stearate, solid polyethylene glycols, sodium lauryl sulfate, and mixtures thereof, and j) sweetening, flavoring, perfuming agents, and mixtures thereof. In the case of capsules, lozenges, tablets and pills, the dosage form may also comprise buffering agents.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed or extended manner. Examples of embedding compositions which can be used include polymeric substances and waxes. Tablet formulations for extended release are also described in U.S. Pat. No. 5,942,244.

Other Products

In addition to pharmaceutical compositions, compounds described herein may be formulated as an elixir, a beverage, a chew, a tablet, a lozenge, a gum, or the like. The compositions may be formulated, for example, as dietary supplements or nutraceuticals.

EXAMPLES

The following examples are provided for illustrative purposes and should not be construed as limiting the scope of the present invention.

Example 1

This example illustrates a method that may be used for the synthesis of 2-(pyridin-3-yl)-2,3,4,7-tetrahydro-1H-azepine.

The above-described synthesis may be used to produce, for example, 10-20 g of 2-(pyridin-3-yl)-2,3,4,7-tetrahydro-1H-azepine, 98% purity by HPLC, Analysis: 13C NMR, 1H NMR, CHN.

Example 2

This example illustrates an alternative method for the synthesis of 2-(pyridin-3-yl)-2,3,4,7-tetrahydro-1H-azepine.

-continued

The literature indicates that compound 5 has been prepared in three steps from commercially available material with yields exceeding 50%. Compound 8 may be prepared by the scheme illustrated above and then alkylated with compound 5 in the same manner. The protective groups are then removed, either sequentially or at the same time to form compound 11, which is cyclized in the same manner of Example 1 to form the target compound 12.

The above-described synthesis may be used to produce, for example, 200 g of 2-(pyridin-3-yl)-2,3,4,7-tetrahydro-1H-azepine, non-cGMP, 98% purity by HPLC, Analysis: 13C NMR, 1H NMR, CHN.

Example 3

This example illustrates in vitro studies of 2-(pyridin-3-yl)-2,3,4,7-tetrahydro-1H-azepine. For these experiments, the mouse macrophage cell line RAW 264.7 was used (referred to herein as RAW). The design of the experiments is the following:

RAW cells were plated in complete medium overnight. The following day, a known inflammatory stimulus (bacterial LPS) was added to the culture wells. Following a 15 minute stimulation, 2-(pyridin-3-yl)-2,3,4,7-tetrahydro-1H-azepine (7-MR) was added to the culture at different concentrations. Twenty-four hours later, RAW cells were harvested and their proteins extracted. Proteins were then run on a polyacrylamide gels and transferred to a nitrocellulose membrane. The membrane was finally probed with commercial antibodies against some classic inflammatory markers. A decrease in the intensity of the protein band indicates that the test compound suppressed the inflammatory markers.

Figure 1:
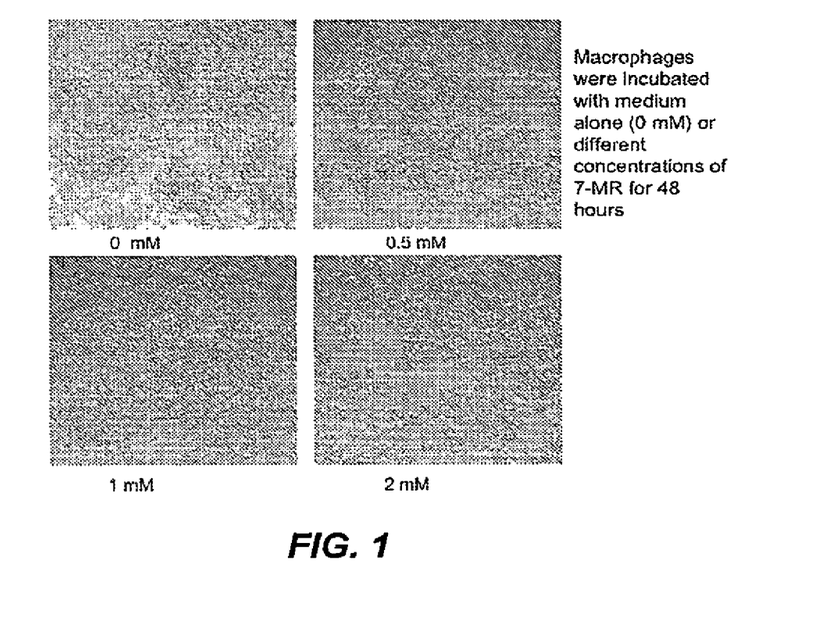
FIG. 1 shows cell viability results for 2-(pyridin-3-yl)-2,3,4,7-tetrahydro-1H-azepine in RAW macrophage cells.
Figure 2:
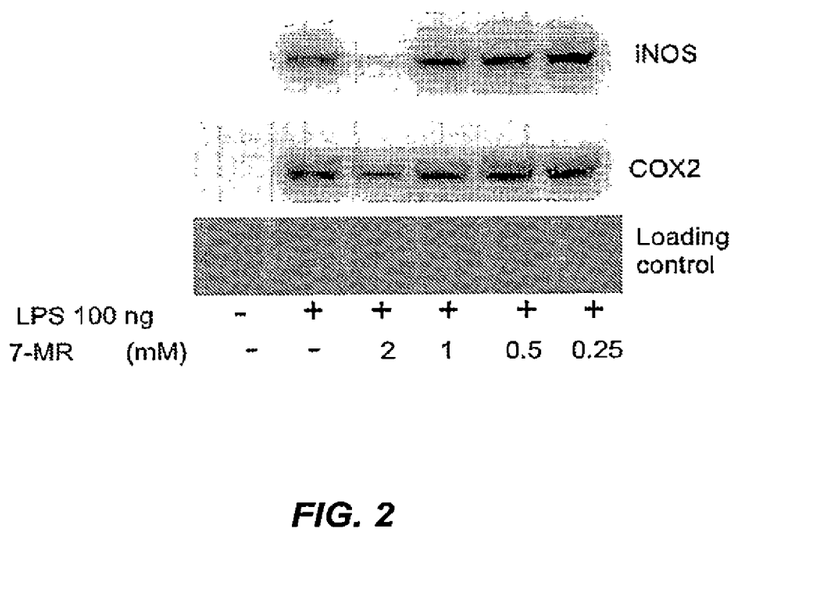
FIG. 2 shows in vitro results of 2-(pyridin-3-yl)-2,3,4,7-tetrahydro-1H-azepine for the inhibition of iNOS and COX2.
Figure 3:
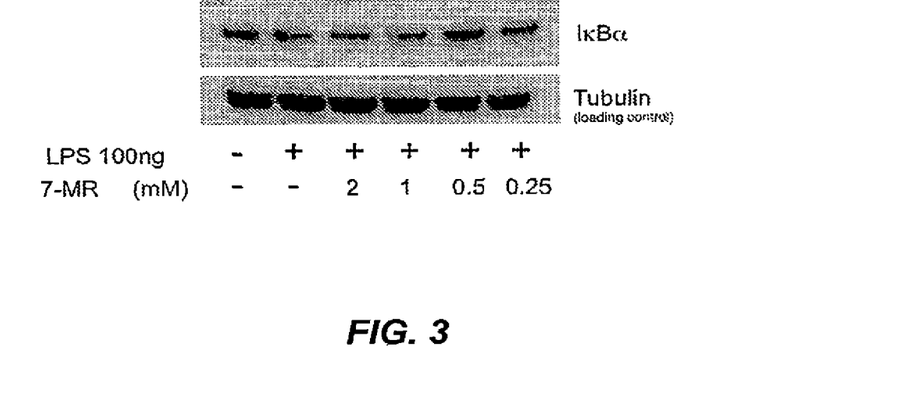
FIG. 3 shows in vitro results of 2-(pyridin-3-yl)-2,3,4,7-tetrahydro-1H-azepine for the inhibition of IκBα.

The following three inflammatory markers were tested:
COX-2 (antibody made by Cayman Chemical, catalog number 160106)
Iκ-B (SantaCruz Biotechnology, sc-371)
iNOS (SantaCruz Biotechnology, sc-650)
Preliminary Test to Assess Cell Viability Before testing the anti-inflammatory effect(s) of 2-(pyridin-3-yl)-2,3,4,7-tetrahydro-1H-azepine, an assay of cell viability was performed. Cell viability results indicated that up to 2 mM, 2-(pyridin-3-yl)-2,3,4,7-tetrahydro-1H-azepine was not toxic to the RAW macrophage cells, as can be seen in FIG. 1. Toxicity was only seen at higher doses (3 mM and above).
Effect on iNOS, COX2, and IkB As can be seen in FIGS. 2 and 3, 2-(pyridin-3-yl)-2,3,4,7-tetrahydro-1H-azepine decreased significantly the expression of iNOS, and slightly that of COX2. It had no effect on NF-kB (as assessed by IkB expression).

Figure 4:
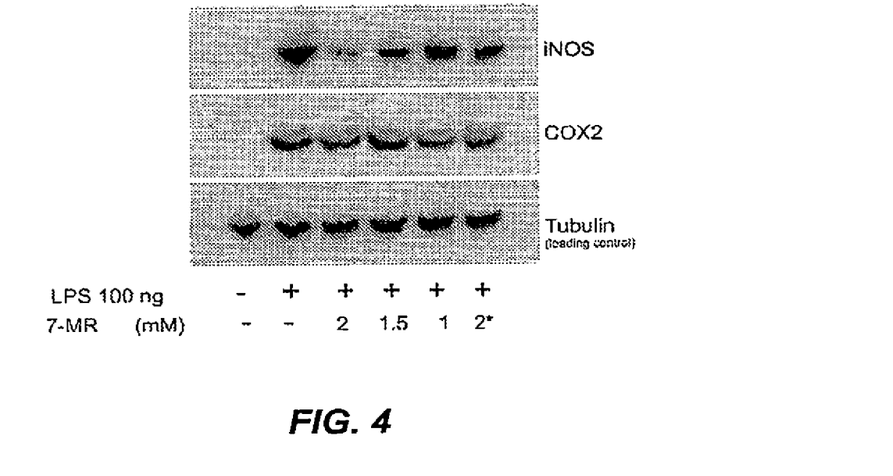
FIG. 4 illustrates the results of separate experiments confirming the ability of 2-(pyridin-3-yl)-2,3,4,7-tetrahydro-1H-azepine to inhibit iNOS expression.

The suppression of iNOS expression was confirmed in separate experiments, as shown in FIG. 4. Overall the results indicate that 2-(pyridin-3-yl)-2,3,4,7-tetrahydro-1H-azepine specifically suppressed iNOS.

Example 4

This example describes experiments for determining monoamine oxidase (MAO) inhibition for 2-(pyridin-3-yl)-2,3,4,7-tetrahydro-1H-azepine and other alkaloids. MAOs are enzymes located on the outer membrane of mitochondria and are involved in the catabolism of monoamine neurotransmitters. There are two well-characterized isoenzymes: MAO-A, which predominantly catabolizes serotonin and norepinephrine, and MAO-B, which preferentially catabolizes benzylamine and phenylethylamine. Dopamine and tyramine are metabolized by both isoforms.

To detect the activity of MAO, a luminescent method (MAO-Glo Assay kit, from Promega, Cat # V1401) was used. In this method, a MAO substrate (a derivative of beetle luciferin provided in the kit) is mixed with the compound to be tested (in this case, myosmine and control compounds). Then, the MAO enzymes (either A or B, purchased separately) are added to the mixture and incubated with the reaction for 1 hour at room temperature. The MAO enzymes, if not inhibited by the test compound, will convert the substrate into methyl ester luciferin. Finally, a luciferin detection reagent (provided by the kit) is added (20 minutes at room temperature) to stop the MAO reaction and convert methyl ester luciferin into D-luciferin. D-luciferin reacts with luciferase to produce a luminescent signal, which is directly proportional to the D-luciferin concentration and thus the MAO activity: the greater the amount of light produced the higher the activity of MAO. The luminescent signal is measured and recorded using a luminometer.

As positive controls for the experiment, clorgyline (a well-characterized potent inhibitor of MAO-A) and deprenyl (a well-characterized potent inhibitor of MAO-B) were used. The compound 2-(pyridin-3-yl)-2,3,4,7-tetrahydro-1H-azepine (7-Member Ring) was tested for its ability to inhibit MAO-A and MAO-B along with the other compounds nornicotine, anabasine, isomyosmine, myosmine, anatabine, and cannabidiol.

Figure 5:
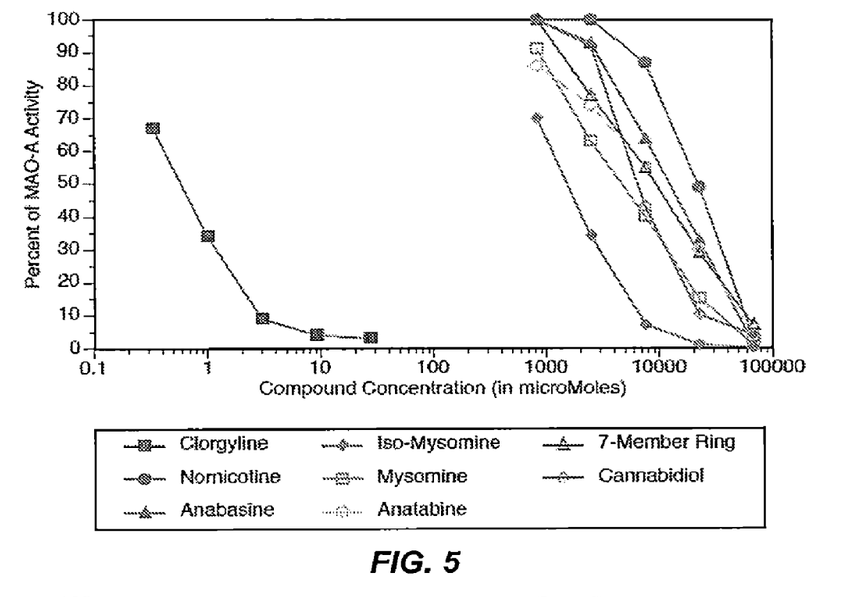
FIG. 5 shows in vitro results of 2-(pyridin-3-yl)-2,3,4,7-tetrahydro-1H-azepine and several other compounds for the inhibition of MAO-A.
Figure 6:
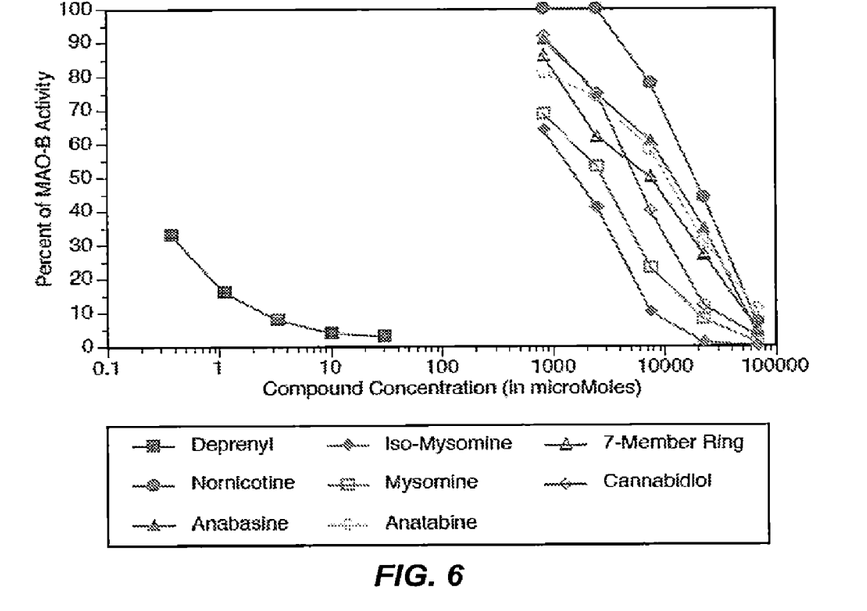
FIG. 6 shows in vitro results of 2-(pyridin-3-yl)-2,3,4,7-tetrahydro-1H-azepine and several other compounds for the inhibition of MAO-B.

FIG. 5 shows that 2-(pyridin-3-yl)-2,3,4,7-tetrahydro-1H-azepine was found to inhibit MAO-A. The way to read this line graph is the following: a 100% activity means that the test compound has no effect on the enzyme; a 0% activity means that the test compound completely kills the enzyme. The more the curve is shifted to the left, the greater the inhibition the test compound exerts on the enzyme. The curve for clorgyline, the positive control for the experiment, is greatly shifted leftward. As shown in FIG. 6, similar results were obtained when testing 2-(pyridin-3-yl)-2,3,4,7-tetrahydro-1H-azepine for the inhibition of MAO-B.

While the invention has been described with respect to specific examples, those skilled in the art will appreciate that there are numerous variations and permutations of the above described systems and techniques that fall within the spirit and scope of the invention as set forth in the appended claims.

What is claimed is:

1. A compound selected from the group consisting of:

2-Pyridin-3-yl-2,3,4,7-tetrahydro-1H-azepine and 2-Pyridin-3-yl-2,3,6,7-tetrahydro-1H-azepine or a pharmaceutically acceptable salt thereof.

2. A compound of claim 1 which is 2-(pyridin-3-yl)-2,3,4,7-tetrahydro-1H-azepine or a pharmaceutically acceptable salt thereof.

3. A composition comprising a compound of claim 2 or a pharmaceutically acceptable salt thereof, and a pharmaceutically acceptable vehicle therefor.

4. A compound of claim 1 which is 2-(pyridin-3-yl)-2,3,6,7-tetrahydro-1H-azepine or a pharmaceutically acceptable salt thereof.

5. A composition comprising a compound of claim 4 or a pharmaceutically acceptable salt thereof, and a pharmaceutically acceptable vehicle therefor.

* * * * *